United States Patent
Woods

(10) Patent No.: US 9,066,989 B2
(45) Date of Patent: *Jun. 30, 2015

(54) SILVER CONTAINING WOUND DRESSING

(71) Applicant: CONVATEC TECHNOLOGIES INC., Las Vegas, NV (US)

(72) Inventor: David Malcolm Woods, Stoney Stanton Leicester (GB)

(73) Assignee: Convatec Technologies Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/280,512

(22) Filed: May 16, 2014

(65) Prior Publication Data

US 2014/0256676 A1 Sep. 11, 2014

Related U.S. Application Data

(63) Continuation of application No. 13/767,656, filed on Feb. 14, 2013, now Pat. No. 8,728,513, which is a continuation of application No. 10/311,674, filed as application No. PCT/GB01/04204 on Sep. 21, 2001, now abandoned.

(30) Foreign Application Priority Data

Sep. 21, 2000 (GB) .................................. 0023155.5

(51) Int. Cl.
*A61F 13/00* (2006.01)
*A61L 26/00* (2006.01)
*A61L 15/18* (2006.01)
*A61L 15/46* (2006.01)
*A61L 15/28* (2006.01)
*A61L 15/44* (2006.01)

(52) U.S. Cl.
CPC ...... *A61L 26/0066* (2013.01); *Y10T 428/24041* (2015.01); *Y10T 442/475* (2015.04); *Y10T 428/24993* (2015.04); *Y10T 442/2525* (2015.04); *Y10T 442/481* (2015.04); *Y10T 442/655* (2015.04); *A61L 15/18* (2013.01); *A61L 15/46* (2013.01); *A61L 2300/104* (2013.01); *A61L 2300/404* (2013.01); *A61L 15/28* (2013.01); *A61L 15/44* (2013.01); *A61L 26/0023* (2013.01)

(58) Field of Classification Search
CPC ......... A61L 15/18; A61L 15/46; A61L 15/28; A61L 15/44; A61L 2300/104; A61L 2300/404
See application file for complete search history.

(56) References Cited

U.S. PATENT DOCUMENTS

| 4,306,551 | A | 12/1981 | Hymes et al. |
| 5,731,083 | A | 3/1998 | Bahia et al. |
| 5,981,821 | A | 11/1999 | Barikosky |
| 6,075,177 | A | 6/2000 | Bahia et al. |
| 6,087,549 | A * | 7/2000 | Flick ............................. 602/41 |
| 6,506,873 | B1 | 1/2003 | Ryan et al. |
| 6,605,751 | B1 * | 8/2003 | Gibbins et al. ................. 602/41 |
| 8,728,513 | B2 * | 5/2014 | Woods .......................... 424/443 |

FOREIGN PATENT DOCUMENTS

| EP | 0243069 | 10/1987 |
| EP | 0707793 | 4/1996 |
| EP | 1318842 | 6/2003 |
| JP | 11-001895 | 1/1999 |
| WO | WO 91/11206 | 8/1991 |
| WO | WO 93/12275 | 6/1993 |
| WO | WO 94/16746 | 8/1994 |
| WO | WO 94/17227 | 8/1994 |
| WO | WO 95/19795 | 7/1995 |
| WO | WO 96/13242 | 5/1996 |
| WO | WO 00/01425 | 1/2000 |
| WO | WO 00/09173 | 2/2000 |

OTHER PUBLICATIONS

Machine translation of JP 11-001,895.*
JP 11-001,895 (English translation cited in the Office action dated Jul. 17, 2014); Minami, Hiroyuki; Jan. 6, 1999.*

* cited by examiner

*Primary Examiner* — Hasan Ahmed
(74) *Attorney, Agent, or Firm* — Convatec Technologies Inc.

(57) ABSTRACT

A wound dressing having anti-microbial activity comprises a first fiber capable of bonding with silver (1) cations. The wound dressing comprises a blend of the first fiber to which silver (1) cations are bonded and a second fiber which is substantially free from silver. The wound dressing comprises from 0.01 to 5.0 percent by weight of silver (1) cations, based on the weight of fiber.

15 Claims, No Drawings

SILVER CONTAINING WOUND DRESSING

CROSS REFERENCES

This application is a continuation of U.S. application Ser. No. 13/767,656 filed Feb. 14, 2013, which is a continuation of U.S. application Ser. No. 10/311,674 filed Dec. 18, 2002, which is a U.S National Stage application of International Application No. PCT/GB01/04204 filed Sep. 21, 2001 which claims priority to GB 0023155.5 filed Sep. 21, 2000.

This invention relates to a wound dressing, in particular to a wound dressing having antimicrobial activity.

International Patent Applications WO 93/12275, WO 94/16746 and PCT/GB99/02093 disclose the carboxymethylation of lyocell fiber and the use of such carboxymethylated fiber in wound dressings.

European Patent Application No. 707,793 discloses a silver-containing antimicrobial agent which comprises carboxymethylcellulose containing silver in an amount of 0.02 to 1 percent by weight and having a degree of substitution of at least 0.4.

Japanese Published Unexamined Patent Application 11-001,895 discloses a hygienic product such as a disposable diaper, sanitary napkin or incontinence pad which comprises water-insoluble carboxymethylcellulose (derived from woodpulp) containing 0.32% by weight silver ions.

The silver-containing fiber used in the prior art dressings discolour (turn dark brown or black) on exposure to light. In consequence, such dressings may exhibit an unsightly appearance. Attempts have been made to overcome this problem and are described for example in International Patent Application WO 00/90173.

It is an object of the present invention to provide a wound dressing in which the above disadvantages are reduced or substantially obviated.

The present invention provides a wound dressing having anti-microbial activity, which comprises a first fiber capable of bonding with silver (1) cations, characterised in that the wound dressing comprises a blend of the first fiber to which silver (1) cations are bonded and a second fiber which is substantially free from silver. The wound dressing according to the invention preferably comprises from 0.01 to 5%, more preferably from 0.1 to 4%, even more preferably from 0.25 to 3% by weight of silver (1) cations, based on the weight of fiber. Most preferably, the wound dressing contains 1 to 2% by weight based on fiber, of silver (1) cations, where the fiber is carboxymethyl cellulose fiber and 0.25% to 0.75% silver (1) cations, where the fiber is an alginate fiber by weight based on the weight of fiber, of silver (1) cations.

The first fiber is preferably substantially insoluble in water and preferably comprises a sodium carboxymethylcellulose fiber, an alginate fiber, a chitosan or chitosan derivative fiber or an acrylic fiber. Where the fiber is a carboxymethylcellulose fiber, it preferably has a degree of substitution between 0.1 and 0.4. Where the fiber is an acrylic fiber, it is preferably an acrylic fiber which incorporates a comonomer such as itaconic acid or 2-acrylamido methyl propane sulphonic acid to provide dye-sites in the fiber.

Where the fiber is an alginate fiber, it may be a calcium alginate fiber or a mixed metal alginate fiber such as a calcium/sodium alginate fiber. The alginate polyemr may be one with a high mannuoronate or a high guluronate.

Wound dressings in which the first fiber is a carboxymethylcellulose fiber are particularly preferred. The second fiber may be similar or different to the first fiber. Similar fibers are preferably used. The second fiber should be such as not to discolour to an objectionable degree in light, and as such should, for example, contain no silver or such low levels of silver that it does not discolour at all or discolours only to a degree which is not objectionable aesthetically.

The ratio of the first silver-containing fiber to the second fiber is preferably in the range from 0.5 to 25% by weight, more preferably 5 to 20% by weight, of the total weight of the fiber.

In order to achieve the desired overall concentration of silver ions, the first fiber preferably includes about 10% by weight, based on the weight of fiber, of silver (1) cations and is blended with a large proportion of unsilvered fiber so as to give a blended product containing the desired weight of silver. The silver ions are preferably chemically bonded to the first fiber.

As specified above, the degree of substitution (D.S.) of the sodium carboxymethylcellulose (CMC) is preferably at least 0.1, and is preferably less than 0.4. Such CMC is inherently insoluble in water and also in saline solution. A higher D.S. gives at least partial solubility in water, which is undesirable in the field to which the invention relates. The D.S. is more preferably in the range from 0.20 to 0.35, for example about 0.3.

The silver ions are preferably introduced into the first CMC fiber by ion-exchange, for example by contacting CMC with an aqueous solution of a salt such as, silver(I) nitrate. As CMC often contains sodium chloride as a by product of the reaction between cellulose and chloroacetic acid and as silver chloride is highly insoluble. It may be preferred to perform the ion-exchange reaction on a salt free grade of CMC. It is preferred that the balance of the carboxyl groups in the CMC be neutralised with sodium ions.

The CMC is preferably derived from lyocell, as disclosed for example in WO 93/12275, WO 94/16746 and PCT/GB99/02093.

The fibrous CMC is preferably in the form of staple fiber or continuous filament yarn. It is preferably contained within a textile article such as a woven, knitted or most preferably a nonwoven fabric, such as a needlepunched nonwoven fabric.

The dressings of the invention are preferably gel-forming, which makes them advantageously low-adherent to wounds and consequently easy to remove. They are soft, conformable and absorbent. Silver metal ions are released slowly over an extended period of time from a wetted dressing of the invention.

The second fiber which does not contain silver is preferably also CMC, but other kinds of gel-forming fiber or of textile fiber may also be utilised. If the dressings are blended from unexposed fiber, on exposure to light, such dressings develop either a speckled appearance or a light brown or light grey colour which is not unsightly. However, it is preferred to pre-expose the silver-containing fiber to light before blending, so that after blending the dressing is light stable and the uniformity of blending can be checked visually.

The wound dressings of the invention may contain other medicaments if desired.

The wound dressings of the invention are useful in the treatment of infected wounds, and as a prophylactic measure against infection of uninfected wounds, also for the reduction or elimination of unpleasant odours produced by wounds.

The invention is illustrated by the following Examples, in which parts and proportions are by weight unless otherwise specified.

Example 1

Manufacture of Master Batch Material

The optimum conditions for manufacture of a master batch material were determined as follows:

Sodium carboxy methyl cellulose fiber (CMC), Hydrocel®, available from Acordis Speciality Fibres Limited of Coventry England, was soaked in silver nitrate ($AgNO_3$) solution in 50 volume % industrial methylated spirit/50 volume % water and the following table shows the percentage silver take-up after soaking, as measured by x-ray fluorescence.

|  | % $AgNO_3$ | |
| --- | --- | --- |
| Conditions | 4% $AgNO_3$ | 8% $AgNO_3$ |
| 15 minutes @ 65° C. | 8.1 | 6.1 |
| 15 minutes @ ambient | 12.6 | 11.2 |
| 4 hours @ ambient | 8.0 | 9.0 |

From the above results, it was determined that higher concentrations of silver nitrate did not appear to be beneficial and that the use of a solution having a concentration of approximately 4% silver nitrate to produce a fiber having a silver content of 8% would give the optimum results. It was therefore decided to produce the master batch material using such a solution.

CMC tow or staple (50g) was added to a solution of 4% silver nitrate (300g) in industrial methylated spirit/water 50/50 at ambient temperature. The solution was held for convenience in a round screw top bottle so that it could be rolled on a laboratory bottle roller. The bottle was rolled for 15 minutes whereupon an ion exchange mechanism took place which produced silver containing CMC-referred to herein as silver CMC (8%w/w, Ag).

The spent silver nitrate solution was discarded and replaced with 50/50 industrial methylated spirit/water wash liquor (300g) followed by shaking for five minutes. This washing process was repeated and finally a soft finish was used. This consisted of 0.5% polysorbate 20 (Tween) 20 in 90:10 industrial methylated spirit/water (i.e. 1.5 g in 300 g).

Excess liquor was squeezed out of the fiber, which was then allowed to dry at ambient temperature. The silver CMC tow was then opened out and spread onto an open bench to allow maximum access to light. The discolouring tow was handled periodically to expose new surfaces to the light. This was continued until the majority of the tow assumed a chocolate brown coloration (about two weeks).

The predominantly brown silver CMC tow produced was blended with untreated carboxymethyl cellulose (CMC) fiber at the ratios shown as follows to produce blends having 0.5%, 1.0% and 2.0% silver:

6.25% silver CMC+93.75% CMC fiber=0.5% Ag
12.5% silver CMC+87.50% CMC fiber=1.0% Ag
25.0% silver CMC+75.00% CMC fiber=2.0% Ag Blending was accomplished by carrying out a carding operation twice to achieve a uniform blend, on hand premixed fiber. The carded web was then cross-folded to give the desired basis weight. The web was then bonded on a needle loom to give a coherent web from which individual dressings were cut. In addition, a conventional carboxymethyl cellulose fiber control sample was manufactured by the same method.

Absorbency Results

The master batch material was produced by the soaking of CMC fiber tow in silver nitrate and the absorbency tests were first of all carried out on tow using a free swell test. It was found that the CMC fiber control had an absorbency of 28 g/g and the silver CMC had an absorbency of 30 g/g. These differences were not considered to be significant.

Absorbency tests were then carried out on fabric produced by needle felting from fibers as above.

Fabric absorbencies as measured by the test identified in the British Pharmacopeia 1993 Addendum 1995 page 1706, Alginate Dressing Absorbency were found to be as shown in the following table, in which gsm=grams per square metre and is a measure of the amount of fabric produced.

|  | gsm | Absorbency g/g | Absorbency g/piece |
| --- | --- | --- | --- |
| CMC control | 111 | 16.0 | 18.0 |
| 0.5% silver CMC | 99 | 20.0 | 19.5 |
| 1.0% silver CMC | 91 | 20.5 | 18.7 |
| 2.0% silver CMC | 65 | 22.3 | 14.5 |

As can be seen from the above table, the addition of silver was found to have very little effect on the absorbency, if anything increasing the absorbency on a gram per gram basis, though having less effect on absorbency on a gram per piece basis.

After wetting for 30 minutes in saline, the fabrics which were initially a fairly dark fawn, changed colour and became lighter and more translucent as time passed.

It appeared that there was no difference in the gelling properties between the CMC and the silver CMC, which is an important observation in that the silver addition does not destroy the valuable gelling properties.

Microbial Activity

To measure the efficiency of the silver containing material in reducing microbial activity, 250 g of milk was mixed with 0.2 g of fiber. The results were as follows:

| Control (milk alone) | Malodour in 2 days |
| --- | --- |
| Control (CMC in milk) | Malodour in 2 days |
| 0.5% Silver (web) | Malodour in 2 weeks |
| 8.0% Silver (tow) | No Malodour in 3 weeks |

These tests were repeated with 0.9 wt. sodium chloride additions (chosen to be equivalent to the salt level in body fluids) to the milk, and the same results were obtained. This shows that the chloride ions in the salt were not detrimental to the antimicrobial properties of the silver in the silver CMC.

As can be seen from the above results, milk alone and milk containing CMC fiber alone went off in two days, as could be easily determined by the smell. By comparison, where the web contained 0.5% silver, there was a two week period before the milk went off and could be smelt. With unblended tow containing 8% silver, no smell could be detected after a three week period when the test was stopped.

In practice, the wound treatment products utilising the invention are unlikely to be left on a wound for more than a few days, and certainly no more than a week, so that it be seen that a blend containing 0.5% silver retains its efficiency in terms of antimicrobial effect for at least twice the period that would be required in practice.

Example 2

A solution of water (33.1 g) and industrial methylated spirit (IMS) (36.0 g) was made up in a black glass bottle suitable for rolling on a bottle roller. To it was added silver nitrate (30.0 g) and the latter was stirred until it dissolved. No heat was required. To this solution was added 12 g of high manuronic calcium alginate tow and the whole was rolled on a bottle roller for four hours. After this period of time the tow was removed and washed in a solution (70 g) containing IMS and water as a 50/50 mixture. Soft finish in the form of polysorbate 20 (0.7 g) was dissolved in (70 g) solution of IMS/water as a 95/5 mixture and the tow was soaked in this medium for approximately 50 minutes. The silver alginate master batch was then dried in a fume cupboard to give a product having 13.7% of silver overall on the fiber.

5 g of the above silver alginate master batch was weighed and cut into staple and opened by hand. 95 g of standard high manuronic calcium alginate fiber was also cut into staple and opened. The two were blended on the in-put feed belt of a laboratory carding machine.

The diluted silver alginate fiber was then carded, cross-folded and needled into a non-woven web. By calculation the final product would contain silver at an average level of 0.6%. It had a light grey-brown flecked mottled appearance.

In a comparative example, the same level (0.68%) of silver was applied uniformly to a batch of the same calcium alginate fiber, and it was then carded, cross-folded, and needled to form a nonwoven web. The web was exposed to light and developed a uniform darkish brown colour, appearing much darker than the mottled appearance of the blended web having the same average amount of silver present.

The invention also contemplates multiple layer dressings some or all of which layers may comprise blended product incorporated silver additions. For example, a silver containing blended layer of a non-gel forming fiber, such as a silver containing acrylic fiber blended with pure acrylic fiber could be faced with a wound contact layer of a gel forming fiber. An example of the contact layer could be an alginate fiber and the alginate layer could be blended with a silver added fiber or may have no silver at all, being a simple gel forming alginate fiber.

The invention claimed is:

1. A wound dressing comprising gel-forming fibers having ant-imicrobial activity, comprising a first fiber which is gel-forming and substantially insoluble in water having silver (I) cations bonded thereto and discoloring on exposure to light, wherein the wound dressing consists of a uniform blend of the first fiber and a second fiber of lyocell which is substantially free from silver, said wound dressing comprising from 0.01 to 5.0 percent by weight of silver (I) cations based on the total weight of first and second fibers, whereby the discoloration of the blend on exposure to light is lessened compared with the discoloration on exposure to light of a batch of the first fiber having the same average amount of silver cations present as is present in the blend.

2. A wound dressing according to claim 1, which comprises from 0.01 to 4.0 percent by weight of silver (I) cations based on the total weight of first and second fibers.

3. A wound dressing according to claim 1, which comprises from 0.25 to 3.0 percent by weight of silver (I) cations based on the total weight of first and second fibers.

4. A wound dressing according to claim 1, wherein the first fiber is selected from a group consisting of a carboxymethylcellulose fiber, an alginate fiber, a chitosan fiber and a chitosan derivative fiber.

5. A wound dressing according to claim 4, wherein the first fiber is a carboxymethylcellulose fiber and the wound dressing contains from 1.0 to 2.0 percent by weight of silver (I) cations, based on the weight of the fiber.

6. A wound dressing according to claim 4, wherein the first fiber is an alginate fiber and the wound dressing contains from 0.25 to 0.75 percent by weight of silver (I) cations, based on the weight of the fiber.

7. A wound dressing according to claim 1, wherein the second fiber contains no silver or low levels of silver such that it discolors to a degree which is not aesthetically objectionable.

8. A wound dressing according to claim 1, wherein the second fiber contains no silver or low levels of silver such that it does not discolor at all.

9. A wound dressing according to claim 1, wherein the ratio of the first fiber to the second fiber is in the range of from 5 to 20% by weight of the total weight of the fiber.

10. A wound dressing according to claim 1, wherein the ratio of the first fiber to the second fiber is in the range of from 0.5 to 25% by weight of the total weight of the fiber.

11. A wound dressing according to claim 1, wherein the first fiber includes at least 8% by weight, based on the weight of the fiber, of silver (I) cations.

12. A wound dressing according to claim 11, wherein the first fiber is prepared using at least a 4% silver nitrate solution.

13. A wound dressing according to claim 1, wherein the silver ions are chemically bonded to the first fiber.

14. A wound dressing according to claim 1, wherein the silver ion are introduced into the first fiber by ion-exchange.

15. A wound dressing according to claim 1, wherein the first fiber having silver (I) cations bonded thereto is pre-exposed to light prior to blending with the second fiber.

* * * * *